United States Patent [19]

Haines

[11] Patent Number: 4,935,005
[45] Date of Patent: Jun. 19, 1990

[54] OPTHALMIC FLUID FLOW CONTROL SYSTEM

[75] Inventor: Stephen W. Haines, Santa Ana, Calif.

[73] Assignee: Nestle, S.A., Ft. Worth, Tex.

[21] Appl. No.: 304,711

[22] Filed: Feb. 1, 1989

Related U.S. Application Data

[60] Division of Ser. No. 105,978, Oct. 6, 1987, Pat. No. 4,832,685, which is a continuation of Ser. No. 865,360, May 21, 1986, abandoned, which is a continuation-in-part of Ser. No. 741,565, Jun. 5, 1985, abandoned.

[51] Int. Cl.⁵ .............................................. A61M 1/00
[52] U.S. Cl. .................................... 604/30; 604/35
[58] Field of Search ..................... 604/22, 27, 28, 30, 604/31, 35

[56] References Cited

U.S. PATENT DOCUMENTS

| | | | |
|---|---|---|---|
| 901,545 | 10/1908 | Morrison . | |
| 2,302,617 | 11/1942 | Little | 285/156 |
| 2,584,206 | 2/1952 | Hodsdon | 285/156 |
| 3,589,363 | 6/1971 | Banko et al. | 128/276 |
| 3,693,613 | 9/1972 | Kelman | 128/24 A |
| 3,812,855 | 5/1974 | Banko | 128/276 |
| 3,902,495 | 9/1975 | Weiss et al. | 128/276 |
| 4,007,742 | 2/1977 | Banko | 128/276 |
| 4,024,866 | 5/1977 | Wallach | 604/22 |
| 4,136,700 | 1/1979 | Broadwin et al. | 128/276 |
| 4,168,707 | 9/1979 | Douvas et al. | 128/276 |
| 4,333,454 | 6/1982 | Hargest, III | 128/214 R |
| 4,340,037 | 7/1982 | Lewicky | 128/1 R |
| 4,395,258 | 7/1983 | Wang et al. | 604/65 |
| 4,493,698 | 1/1985 | Wang et al. | 604/51 |
| 4,496,342 | 1/1985 | Banko | 604/22 |

Primary Examiner—Jerome L. Kruter
Attorney, Agent, or Firm—Vorys, Sater, Seymour & Pease

[57] ABSTRACT

A fluid flow control apparatus specially adapted for use with an ultrasonic surgical tool which provides for irrigation of a surgical site and for aspirating fluid from the site comprises a source of irrigation fluid, comprises an irrigation fluid conduit for conducting the irrigation fluid to a surgical site, an aspiration fluid conduit for conducting fluid away from the surgical site, a suction pump connected to the aspiration fluid conduit for aspirating fluid from the surgical site, a pressure-sensitive control system for removing the source of suction from the aspiration conduit when a predetermined value of suction is exceeded, and a valve for controllably admitting irrigation fluid into the aspiration fluid conduit. A check valve in the irrigation conduit prevents a reverse surge when the irrigation fluid is admitted to the aspiration conduit.

4 Claims, 2 Drawing Sheets

OPTHALMIC FLUID FLOW CONTROL SYSTEM

This is a divisional of co-pending application Ser. No. 07/105,978 filed on Oct. 6, 1987 (U.S. Pat. No. 4,832,685 issued Apr. 23, 1989) which is a continuation of Ser. No. 06/865,360 filed May 21, 1986 now abandoned and which was a continuation-in-part application of Ser. No. 06/741,565, now abandoned.

BACKGROUND OF THE INVENTION

1. Field of the Invention:

This invention relates to fluid control systems for surgical irrigation and aspiration and more particularly to fluid control systems for use with an ultrasonic surgical tool which includes means for irrigation of a surgical site and means for aspiration of fluid from the surgical site.

2. Description of the Prior Art:

Intraocular surgery, and removal of cataracts in particular, has been greatly aided by the development of surgical instruments which include cutting or fragmenting means combined with means for irrigating the intraocular surgical site and aspirating therefrom the irrigating fluid together with any tissue fragments produced by the surgical procedure. One instrument of this type is disclosed in U.S. Pat. No. 3,589,363, to Banko et al. The surgical instrument therein disclosed comprises a handpiece which holds an elongated ultrasonic surgical tool and contains means for exciting longitudinal ultrasonic vibrations in the tool. The vibrating tool when applied to a tissue such as the crystalline lens of the eye which has developed a cataract is capable of breaking the tissue into small pieces. The tool is provided with means for supplying an irrigating fluid to the surgical site and aspiration means for removing irrigation fluid and fragmented tissue from the surgical site. The aspiration means includes an axial bore through the ultrasonic tool which is connected to a source of suction whereby the tissue fragments are aspirated from the surgical site, together with the irrigation fluid. Because the ultrasonic surgical tool of this patent fragments the excised tissue into very small particles, which are removed with the spent irrigation fluid, the incision in the eyeball need be only large enough to insert the tool and is substantially smaller than the incision required for removing the lens in one piece. However, since the surgical wound in the eyeball is only large enough to insert the ultrasonic surgical tool and irrigation means, the surgical field is practically entirely enclosed, and controlling the flow of irrigation fluid and aspiration fluid is very important. In particular, the suction applied to the aspiration means must be limited to a safe value, to avoid the danger of collapsing the eyeball. The fluid control system disclosed by Banko et al. is operated by the surgeon and comprises an aspiration pump and electrically operated valve means for connecting and disconnecting the suction inlet of the pump to the aspiration tubing which conveys fluid away from the surgical field. The valve is controlled by the surgeon by means of a foot switch.

An improved fluid control system is disclosed by Kelman, U.S. Pat. No. 3,693,313. This apparatus addresses the problem of maintaining the proper pressure in the enclosed surgical field even with the occurrence of blockages in the aspiration conduit. A blockage or the occlusion may occur, for example, when a piece of fragmented tissue which is larger than the axial bore of the surgical tool is drawn against the entrance to the axial bore in the tool. When such a blockage occurs in the aspiration line, the negative pressure or suction in the aspiration conduit between the surgical site and the vacuum pump increases. If the blockage is then suddenly released either by the mechanical action of the ultrasonic tool or by the increased value of the suction force, there is a tendency for the fluid within the surgical site to rush suddenly into the aspiration conduit with perhaps disastrous consequences. This is an especially important problem in ocular surgery because the total volume of the fluid in the surgical site is smaller than the volume of fluid in the irrigation and aspiration lines. Accordingly, the flow control system of Kelman, U.S. Pat. No. 3,693,613 provides for automatic rapid equalization of the pressure in the aspiration conduit when occlusion is removed. This is accomplished by providing a flow-sensitive transducer in the aspiration conduit which senses the rate of fluid flow and generates an electrical signal which is sent to a controller. Whenever the flow rate increases suddenly, indicating that a blockage has just been cleared, the controller causes a vent valve in the aspiration conduit to open at once, thus relieving the suction and preventing excessive withdrawal of fluid from the surgical site.

The flow control system of Kelman, U.S. Pat. No. 3,693,613 is effective but somewhat complicated. Accordingly, another flow control system for surgical devices of this type was developed by Weiss, et al., U.S. Pat. No. 3,902,495. In this system irrigation fluid is supplied to the surgical site from a source of fluid via an irrigation conduit provided with a pressure relief valve to prevent the irrigation pressure from becoming too high. Similarly, the aspiration conduit is provided with a relief vent valve which opens to the atmosphere at a preset pressure differential, thereby preventing the suction in the aspiration conduit from exceeding a preset value. In this way, the suction in the aspiration line never exceeds a predetermined preset value, and the surgical site is not exposed to excess suction when a blockage is cleared.

Another variation of the method of U.S. Pat. No. 3,693,613 is disclosed in Banko, U.S. Pat. No. 4,496,342. In Banko's apparatus irrigation fluid is supplied to an enclosed surgical site such as the interior of the eye and withdrawn from the surgical site through an aspiration conduit. A flow-sensitive transducer in the aspiration conduit senses the sudden increase in flow rate which occurs when a blockage in the aspiration tube is released and actuates a valve which releases fluid from a second source of fluid into the aspiration line. At the same time, the aspiration pump is shut off until the flow rate has returned approximately to normal. In this way the surge of fluid out of the eye when an aspiration line blockage is released is greatly diminished.

While these flow control systems are effective, they have not addressed the problem of releasing the blockage itself. At best they have limited the suction to a maximum value or sensed the flow surge after the blockage is released and reduced the surge. They have not incorporated the capability of sensing the blockage and then rapidly and positively, under control of the surgeon, equalizing the pressure in the irrigation and aspiration lines for rapid clearing of a blockage.

Hence a need has continued to exist for a fluid control system for a surgical irrigator/aspirator wherein the excess vacuum in the aspiration tubing after a blockage can be controllably and rapidly released.

SUMMARY OF THE INVENTION

An apparatus has now been developed which provides for rapid controllable release of the pressure in the aspiration line when an occlusion of the line occurs. The apparatus of this invention comprises a source of irrigation fluid, irrigation fluid conduit means for conducting the irrigation fluid to a surgical site, aspiration fluid conduit means for conducting fluid away from the surgical site, suction means in fluid communication with the aspiration fluid conduit means for aspirating fluid from the surgical site, pressure-sensitive control means for removing the source of suction from the aspiration conduit when a predetermined value of suction is exceeded, and means for controllably admitting irrigation fluid into the aspiration fluid conduit.

The invention also comprises a special modified T-connection fitting for conveniently connecting the fluid conduits used in the fluid flow control system.

Accordingly, it is an object of the invention to provide an apparatus for irrigation and aspiration of an enclosed surgical site.

A further object is to provide apparatus for controllably releasing blockages in a surgical aspiration conduit.

A further object is to provide apparatus for rapidly releasing suction in the aspiration line of a surgical aspirator.

A further object is to provide apparatus for rapidly equalizing pressure in a surgical irrigation-aspiration system in order to remove occluding matter.

A further object of the invention is to provide a method for controllably clearing blockages in a surgical irrigation-aspiration system by equalizing pressure in the irrigation and aspiration conduits.

A further object is to provide a fluid connecting fixture for conveniently connecting fluid conduits providing irrigation, aspiration, and pressure sensing in a surgical irrigation-aspiration system.

Further objects of the invention will become apparent from the description of the invention which follows.

BRIEF DESCRIPTION OF THE DRAWINGS

The nature and advantages of the invention will be better understood when the detailed description of the invention is considered in conjunction with the drawings provided, wherein.

DETAILED DESCRIPTION OF THE INVENTION AND PREFERRED EMBODIMENTS

Figure 1:
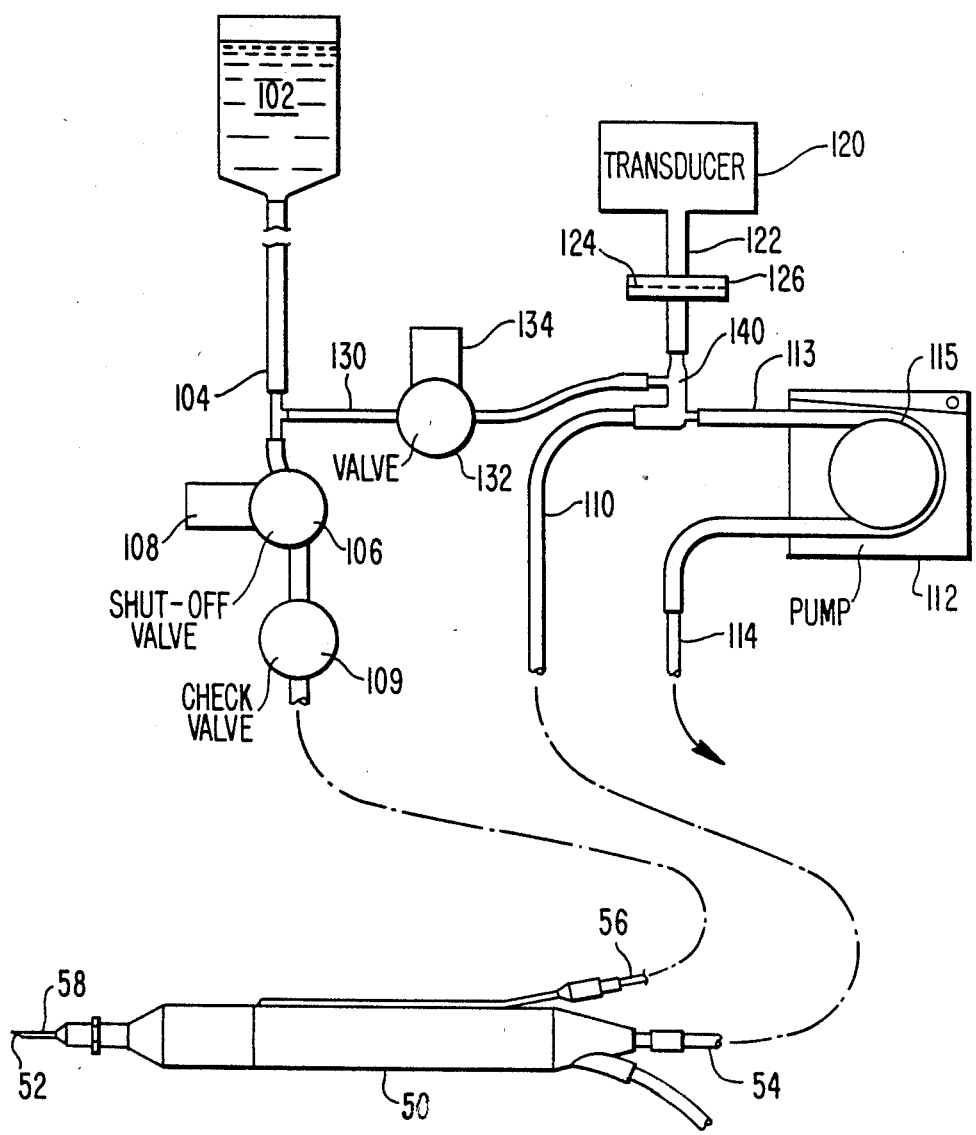
FIG. 1 illustrates schematically a fluid control system for a surgical irrigator/aspirator.

The invention will now be described with reference to a preferred embodiment thereof illustrated in FIG. 1. The flow control system is illustrated as associated with an ultrasonic surgical handpiece 50 of the type described in U.S. Pat. No. 3,589,363, but it will be understood that the flow control system is adaptable to any surgical irrigation-aspiration system and is of great utility wherever occlusion of the aspiration system can occur. The surgical handpiece 50 is provided with an ultrasonic tool 52 having an axial suction passage connected to an aspiration tube 54. Irrigation fluid is supplied through tube 56 and is directed to the surgical site through a passage coaxial with the ultrasonic tool 52 and defined by sheath 58.

A source of irrigation fluid 102 supplies fluid through irrigation conduit 104 to the irrigation fluid supply tube 56 of the handpiece 50. The source of irrigation fluid 102 may be a conventional bottle or bag of irrigating fluid, e.g., a conventional ophthalmological irrigating fluid for ocular surgery, suspended above the surgical site at an elevation to supply the desired irrigation pressure. This pressure will typically range from 10 mm Hg to 100 mm Hg, preferably 30 mm Hg to 60 mm Hg, for surgical procedures in the anterior chamber of the eye. A shut-off valve 106 is provided in the irrigation conduit to control the starting and stopping of the irrigation. Preferably this shut-off valve 106 is a remotely controllable valve, e.g., an electrically controlled valve operated by a solenoid 108.

The fluid withdrawn from the surgical site through the aspiration tube 54 is drawn through the aspiration conduit 110 of the flow control system by vacuum pump 112 and is, discharged through waste conduit 114 to a waste container which is not shown. The vacuum pump 112 is shown as a peristaltic pump having a pump tube 113 and a rotor 115. Such a pump is preferred in this invention because of its lack of contamination, its good controllability, its relatively high suction capability, and the ease with which the pump may be stopped without special provision for avoiding backflow. However, any appropriate source of vacuum may be used, with the understanding that the control means for disconnecting the source of vacuum from the aspiration line, discussed more fully below, will have to be adapted to the needs of each type of pumps. For example, while a peristaltic type pump may be stopped by simply turning off its drive motor and thereupon inherently preventing backflow, other types of pump may require auxiliary valves to disconnect the source of suction from the aspiration conduit.

According to the method for eliminating occlusions of this invention, the source of vacuum is immediately stopped or disconnected from the aspiration conduit 110 as soon as the vacuum exceeds a predetermined level, which indicates that an occlusion of the aspiration bore in the ultrasonic tool 52 has occurred. For this purpose a pressure sensitive transducer 120 is arranged in fluid transmissive contact with the aspiration conduit 110. Ordinarily the transducer will be connected to the aspiration conduit 110 by a short length of tubing 122 connected to the aspiration conduit 110 by means of a special connecting fitting 140. A hydrophilic-hydrophobic filter 124 mounted in a filter holder 126 is inserted between the aspiration conduit 110 and the transducer connecting tubing 122 in order to protect the transducer from contamination by contact with tissue particles and the like carried along with the aspiration fluid.

The pressure sensitive transducer 120 generates an electrical signal proportional to the vacuum in the aspiration conduit 110 induced by the pump 112. This signal is used to control the pump 112, so that the source of vacuum for the aspiration conduit 110 is quickly removed when the vacuum exceeds the predetermined value, thereby indicating that an occlusion has occured. In its simplest form, the pressure-sensitive transducer 120 may be a simple pressure switch which turns off the motor (not shown) of the peristaltic pump 112. When a peristaltic pump is used it is only necessary to turn off the drive motor to stop the pump, maintain the suction vacuum at the level it had reached, and prevent backflow of waste irrigation fluid. It will be recognized that it is also possible to use a continuously running pump with a controllable shut-off valve between the pump and the aspiration conduit 110. With such an apparatus, the signal from the pressure sensitive transducer 120 will cause the shut-off valve to be closed, thereby preventing the vacuum from increasing, but also holding the aspiration conduit at the level of vacuum reached before disconnection. A shut-off valve may also be necessary if a pump is used which cannot prevent backflow when it is shut off.

When the source of vacuum has been disconnected from the aspiration conduit 110, e.g., by stopping the pump 112, it is desirable to equalize the pressure in the irrigation and aspiration lines as soon as possible in order to release the blockage. When the pressures are so equalized, any suction force holding a tissue fragment against the aspiration inlet of the ultrasonic tool 52 is removed, and the tissue fragment can be easily dislodged. In the apparatus of this invention the pressure equalization is accomplished by means of pressure equalizing conduit 130, which conducts fluid from the source of irrigation fluid 102 to the aspiration conduit 110. Valve 132 in pressure equalizing conduit 130 controls the flow of fluid through conduit 130. Valve 132 is normally closed when the apparatus is being used to aspirate fluid and tissue from a surgical site. When a blockage occurs in the aspiration conduit 110, e.g., when a tissue fragment occludes the axial bore in the ultrasonic tool 52, the increased suction in the aspiration line 110 will be sensed by the pressure-sensitive transducer 120 which will in turn send a signal which shuts off the pump 112. Thereupon, the surgeon can release the vacuum in the aspiration conduit 110 by opening the valve 132 to admit irrigation fluid from the source of irrigation fluid 102 to the aspiration fluid conduit 110 via a pressure equalizing conduit 130 which is connected to the aspiration conduit 110 through the special fitting 140. Since the entire system is filled with liquid, the pressure equalization is very rapid, more rapid than in systems which adjust pressure by admitting air to the system. As soon as the pressure has been equalized, the transducer 120 will detect the lower level of suction and restart the pump. However, as long as valve 132 is open fluid will flow directly from the source of irrigation fluid 102 to aspiration conduit 110 and no substantial amount of aspiration will be applied to the surgical site through the suction conduit. When the valve 132 is closed the pump 112 will again draw fluid from conduit 110 and suction will thereby be reapplied to the surgical site.

It is greatly preferred that valve 132 be a remotely controlled valve, for example an electrically controlled valve actuated by a solenoid indicated schematically as 134. The solenoid 134 is energized by a source of electrical power under control of a switch operated by the surgeon. Preferably the switch is a foot switch so that the surgeon can easily equalize the pressure and dislodge occluding tissue without having to remove his hands from performing the surgical procedure. A check valve 109 is provided in irrigation supply tube 56 to prevent a backward surge of fluid in the irrigation supply tube 56 when valve 132 is opened to permit irrigation fluid to flow into the aspiration conduit.

Figure 2:
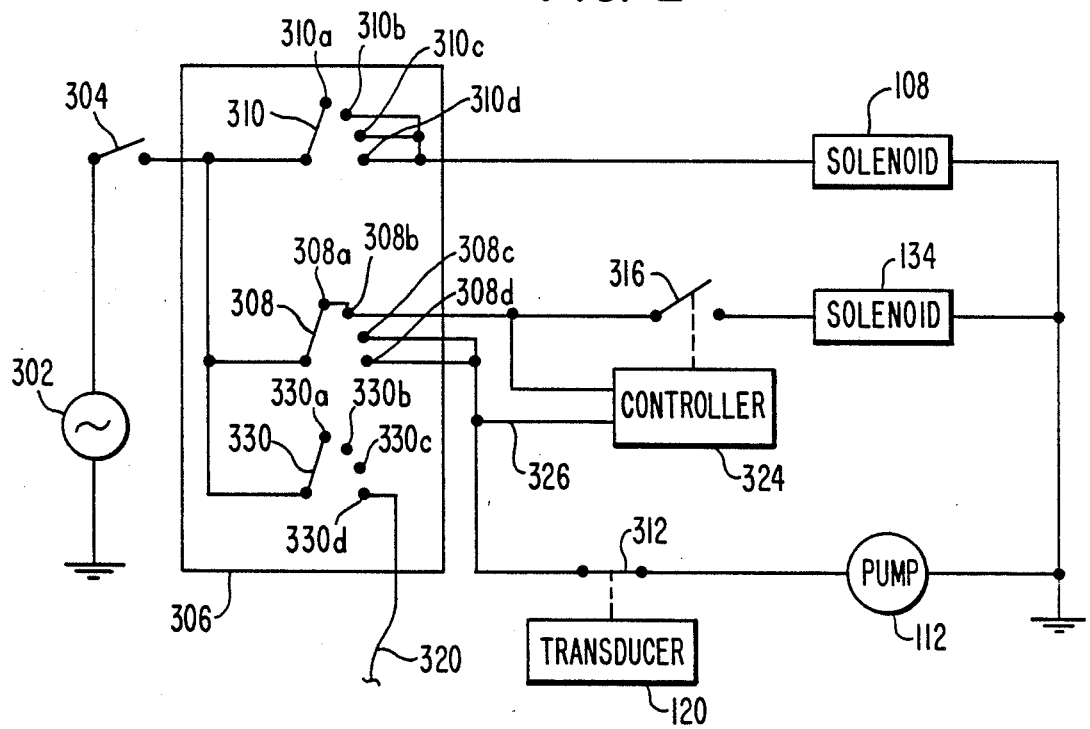
FIG. 2 illustrates an electrical control system for operating the fluid control system of the invention.

A schematic electrical circuit which can be used to control the flow control system of the invention is illustrated in FIG. 2. A source of electrical energy 302, e.g., conventional line current, is supplied to operate the electrical controls of the apparatus. Master switch 304 turns on the apparatus and supplies power to footswitch 306, having four positions, designated as positions zero through three The foot switch 306 is provided with at least three movable contacts 308 and 310 each having an off position 308a and 310a respectively, corresponding to position 0 of the footswitch, and each movable contact engaging stationary contacts 308b–d, 310b–d corresponding to positions 1–3, respectively, of the footswitch The footswitch is biased so that when no foot pressure is exerted thereon the switch is in position 0, the position shown, wherein contacts 308, 310 are in off positions 308a, 310a, and no power is connected to the control circuitry. Accordingly, solenoids 108 and 134 are not energized and valves 106 and 132 are closed to prevent irrigation fluid flow When the footswitch 306 is depressed to position 1, contacts 308b and 310b are energized. Accordingly, solenoid 108 is energized to open valve 106 to supply irrigation fluid to the surgical handpiece 50. However, solenoid 134 is not energized because switch 316 is in its normally open position, and therefore valve 132 remains closed Pump 112 is deactivated in footswitch position 1. When footswitch 306 is further depressed to position 2, contacts 308c and 310c are energized. Solenoid 108 remains energized, and accordingly, valve 106 remains open to supply irrigation fluid. Solenoid 134 is disconnected, and therefore valve 132 cannot open when the footswitch is in this position. Pump 112 is energized via normally closed switch 312 which is under the control of pressure transducer 120. This control may be mechanical or electrical as is well known to those skilled in the art. Accordingly, pump action fills aspiration conduit 110 with irrigation fluid. Switch 312 will be normally closed when the suction in the aspiration conduit 110 does not exceed a predetermined value, and will open when that value is exceeded. At the start of the surgical procedure, footswitch 306 will be depressed to position 3 to energize the ultrasonic surgical tool via wire 320 leading to the ultrasonic generator and control circuits for the handpiece which are entirely conventional and are not shown. The surgeon now proceeds with ultrasonic cutting using the 52 in handpiece 50 During the normal course of the surgical procedure, the switch 312 will be closed so that the pump 112 provides a source of suction on for aspirating fluid and fragmented tissue from the surgical site, while irrigation fluid is through open valve 106. The pressure equalizing conduit remains closed normally. When an occlusion occurs, the vacuum aspiration conduit 110 increases and pressure-sensitive 120 causes switch 312 to open, shutting off pump 312. The will ordinarily be alerted to the occurrence of a blockage when the sound of the operating pump motor stops. He may, of course, also observe it through his operating microscope, or a alarm, also operated by the pressure-sensitive may be provided. The surgeon thereupon can equalize the by raising his foot, and moving footswitch 306 from 3 to position 1, thus allowing the footswitch contacts to return to the position wherein contacts 308b and 310b are energized. When the footswitch 306 makes the transition from position 2 to position 1 triggered controller 324, which controls switch 316 is activated and momentarily opens switch 316. Triggered controller 324 receives power via contact of the switch 306 and may include a conventional single-pulse circuit, e.g., a one-shot multivibrator, which supplies single pulse to an actuator, e.g., a relay coil, which momentarily closes switch 316. The single-pulse circuit may be via connection 326 when the footswitch 306 moves from 2 to position 1. The triggered controller 324 and circuitry are conventional and readily implemented by one in the art. Solenoid 134 is thus momentarily actuated by 316 to open valve 132 in pressure equalizing conduit to admit irrigation fluid directly from the source of irrigation fluid 102 into the aspiration conduit 110 to re the suction in conduit 110. With the removal of the in aspiration conduit 110, no suction force holds tissue at the entrance of the axial bore in the ultrasonic tool and the fragments may easily be dislodged. The surgeon may continue the procedure by depressing the foot switch 2 and 3. Valve 132 is by this time closed and to the aspiration conduit 110. While the des control system represents one circuit which accomplishes the objects of the invention, it will be recognized that alternate circuits may be employed.

Figure 3:
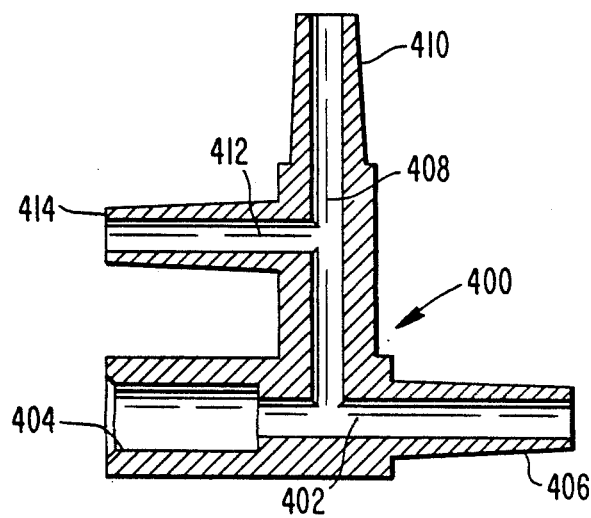
FIG. 3 illustrates a fluid connecting fitting specially adapted for connecting aspiration conduit, pressure relief conduit and pressure sensing conduit in the surgical irrigation-aspiration system of this invention.

The invention also encompasses a special fitting 400 shown in cross section in FIG. 3. This connecting fitting is specially adapted to fulfill of connecting together the aspiration conduit, the pressure relief conduit and the pressure-sensitive transducer. The fitting comprises a first tubular fluid conduit 402 having a female connecting member 404 at one end for receiving the aspiration tubing 110 coming from the handpiece 52. This tubing carries aspirated fluid together with fragmented tissue, and the connection provides a smooth internal wall for the conduit in order to reduce the chance of clogging. The tubular conduit 402 is provided at its other end with a male connecting member 06 for connecting to the tubing 113 leading to the source of e.g., pump 112. A second rigid tubular fluid conduit 408, in communication with the first tubular conduit 402 between end connecting members 404 and 406, is arranged generally at right angles to the first conduit 402. The second fluid has a male tapered connecting member 410 at its free end to mate with a female tapered connecting fitting on the fi housing 126 or with tubing 122 leading to the transducer 120. A third rigid fluid conduit 412 has one end to and in fluid communication with the fluid conduit 408 at a point intermediate between its end. The other end 414 of the third tubular conduit 412 is tapered to receive the end of the pressure equalizing conduit 130. The third fluid conduit 412 is arranged generally at right angles to second tubular conduit 408 and parallel to the first tubular conduit 402. This special connecting fitting 400 permits the rapid and convenient connection of all the fluid conducting members associated with the pressure equalizing the apparatus of this invention.

The invention having been fully described, it should be understood that it may be in other specific forms or variations without departing its spirit or essential characteristics. Accordingly, the embodiments described above are to be considered in all respects as illustrative and not restrictive, the scope of being indicated by the appended claims rather than foregoing description, and all changes which come within the meaning and range of equivalency of the claims are intended to embrace therein.

What is claimed is:

1. A fluid control apparatus for use with a surgical irrigation and aspiration instrument adapted for irrigation and aspiration of a surgical site located in a small elastic chamber, said fluid control apparatus comprising:

an irrigation fluid conduit means including valve means for conducting irrigation fluid from a single source of irrigation fluid to the surgical site,
an aspiration fluid conduit means operatively connected to a source of vacuum for removing fluid from the surgical site,
a single controllable pump means in fluid communication with said aspiration fluid conduit means for providing suction in said aspiration fluid conduit means, and
a pressure sensitive transducer means in fluid communication with said aspiration fluid conduit means for generating, when said controllable pump means is pumping, a pump control signal for said controllable pump means proportional to the rise in vacuum in said aspiration fluid conduit means induced by said pump means, and said transducer means sensing a vacuum rise in said aspiration fluid conduit means and,
a liquid pressure equalizing means for admitting irrigation liquid from the single source of irrigation liquid when said valve means is opened to said aspiration fluid conduit means when a blockage occurs therein to vent the vacuum therein so as to remove the blockage, said pressure equalizing means allowing the equalizing of the pressure in said aspiration and irrigation conduit means.

2. A fluid control apparatus for use with a surgical irrigation and aspiration instrument adapted for irrigation and aspiration of a surgical site located in a small elastic chamber, said fluid control apparatus comprising:

an irrigation fluid conduit means including valve means for conducting irrigation fluid from a single source of irrigation fluid to the surgical site,
an aspiration fluid conduit means for removing fluid from the surgical site,
a suction means in fluid communication with said aspiration fluid conduit means for providing suction in said aspiration fluid conduit means,
a pressure sensitive transducer means in fluid communication with said aspiration fluid conduit means for generating, when said controllable pump means is pumping, a pump control signal for said controllable pump means proportional to the rise in vacuum in said aspiration fluid conduit means induced by said pump means, and said transducer means sensing a vacuum rise in said aspiration fluid conduit means and for disconnecting said aspiration fluid conduit means from the source,
a liquid pressure equalizing means for admitting irrigation liquid from the single source of irrigation liquid when said valve means is opened to said aspiration fluid conduit means when a blockage occurs therein to vent the vacuum therein so as to remove the blockage, and
said liquid pressure equalizing means including a pressure equalizing conduit providing communication for the irrigation liquid from the single source of irrigation liquid to said aspiration fluid conduit means, said pressure equalizing means allowing the equalizing of the pressure in said aspiration and irrigation conduit means.

3. The apparatus of claim 2 wherein the source of irrigation fluid comprises a bottle containing the irrigation fluid and is positioned generally above the surgical site.

4. The apparatus of claim 2 wherein the source of irrigation fluid comprises a bag containing the irrigation fluid and is positioned generally above the surgical site.

* * * * *

(12) EX PARTE REEXAMINATION CERTIFICATE (5841st)
United States Patent
Haines

(10) Number: US 4,935,005 C1
(45) Certificate Issued: Aug. 7, 2007

(54) OPTHALMIC FLUID FLOW CONTROL SYSTEM

(75) Inventor: Stephen W. Haines, Santa Ana, CA (US)

(73) Assignee: Nestle S.A., Alcon Laboratories, Inc., Fort Worth, TX (US)

Reexamination Request:
No. 90/007,405, Jan. 31, 2005
No. 90/007,506, Apr. 8, 2005

Reexamination Certificate for:
Patent No.: 4,935,005
Issued: Jun. 19, 1990
Appl. No.: 07/304,711
Filed: Feb. 1, 1989

Related U.S. Application Data

(60) Division of application No. 07/105,978, filed on Oct. 6, 1987, now Pat. No. 4,832,685, which is a continuation of application No. 06/865,360, filed on May 21, 1986, now abandoned, which is a continuation-in-part of application No. 06/741,565, filed on Jun. 5, 1985, now abandoned.

(51) Int. Cl.
*A61M 1/00* (2006.01)

(52) U.S. Cl. .......................................... 604/30; 604/35

(58) Field of Classification Search .................... 604/30
See application file for complete search history.

(56) References Cited

U.S. PATENT DOCUMENTS

| | | | |
|---|---|---|---|
| 3,920,014 A | 11/1975 | Banko |
| 4,019,514 A | 4/1977 | Banko |
| 4,496,342 A | 1/1985 | Banko |
| 4,832,685 A | 5/1989 | Haines |

*Primary Examiner*—Beverly M. Flanagan

(57) ABSTRACT

A fluid flow control apparatus specially adapted for use with an ultrasonic surgical tool which provides for irrigation of a surgical site and for aspirating fluid from the site comprises a source of irrigation fluid, comprises an irrigation fluid conduit for conducting the irrigation fluid to a surgical site, an aspiration fluid conduit for conducting fluid away from the surgical site, a suction pump connected to the aspiration fluid conduit for aspirating fluid from the surgical site, a pressure-sensitive control system for removing the source of suction from the aspiration conduit when a predetermined value of suction is exceeded, and a valve for controllably admitting irrigation fluid into the aspiration fluid conduit. A check valve in the irrigation conduit prevents a reverse surge when the irrigation fluid is admitted to the aspiration conduit.

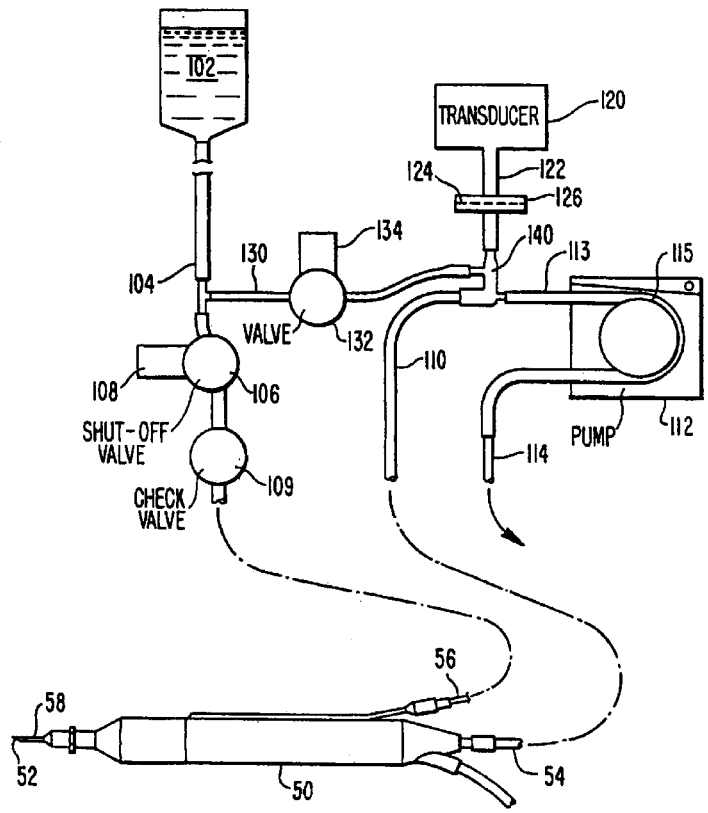

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–4 are cancelled.

* * * * *